United States Patent

Deckers et al.

[11] Patent Number: 5,320,833
[45] Date of Patent: Jun. 14, 1994

[54] ARYLPOLYENECARBOXYLIC ACIDS AND THEIR DERIVATIVES AS SUNSCREEN AGENTS IN COSMETIC PREPARATIONS

[75] Inventors: Gabriele Deckers, Ludwigshafen; Rainer Becker, Bad Durkheim; Bernd Wenderoth, Lampertheim; Norbert Goetz, Worms; Karin Sperling-Vietmeier, Neustadt, all of Fed. Rep. of Germany

[73] Assignee: BASF Aktiengesellschaft, Ludwigshafen, Fed. Rep. of Germany

[21] Appl. No.: 764,212

[22] Filed: Sep. 23, 1991

[30] Foreign Application Priority Data

Nov. 17, 1990 [DE] Fed. Rep. of Germany ....... 4036779

[51] Int. Cl.$^5$ ............ A61K 7/42; A61K 9/10; A61K 9/14; C07D 317/44
[52] U.S. Cl. .................... 424/59; 424/47; 424/60; 424/69; 514/844; 514/847; 514/938; 514/939; 514/944; 549/446; 549/447
[58] Field of Search ........................... 424/59

[56] References Cited

U.S. PATENT DOCUMENTS

4,387,089  6/1983  De Polo ........................ 424/59

FOREIGN PATENT DOCUMENTS

0169571  1/1986  European Pat. Off. ....... C07F 9/02
2728242  1/1979  Fed. Rep. of Germany .
2945125  5/1980  Fed. Rep. of Germany .
3206586  7/1983  Fed. Rep. of Germany .

OTHER PUBLICATIONS

Haensel et al, Chem. Abs., 1967, vol. 67, 84918z.
Scarbrough et al, Chem. Abs., 1974, vol. 81, 55340p.
Israili et al, Chem. Abs., 1977, vol. 86, 5263y.
Chem. Abs., 1981, vol. 95, 124092n.
Koppel et al, Chem. Abs., 1991, vol. 114, 114567e.

*Primary Examiner*—Dale R. Ore
*Attorney, Agent, or Firm*—Oblon, Spivak, McClelland, Maier & Neustadt

[57] ABSTRACT

Arylpolyenecarboxylic acids and their derivatives of the formula I $$Ar\text{---}(CR^7\text{=}CR^6)_{\overline{n}}CR^5\text{=}CR^4\text{---}\underset{\underset{OR^2}{|}}{C}\text{=}CR^3\text{---}COOR^1 \qquad I$$

where
Ar is phenyl, biphenylyl or naphthyl, each of which can be substituted by one to three $C_1$–$C_4$-alkyl, $C_1$–$C_4$-alkoxy, hydroxyl or phenoxy groups, or amino groups which can be mono- or di-substituted by $C_1$–$C_4$-alkyl groups, or one methylenedioxy group, it being possible for the substituents to be identical or different,
$R^1$ is hydrogen, an alkali metal or ammonium cation, $C_1$–$C_{20}$-alkyl or $C_2$–$C_{20}$-alkenyl,
$R^2$ is $C_1$–$C_8$-alkyl,
$R^3$ to $R^7$ are each hydrogen or $C_1$–$C_4$-alkyl, and
n is 0 or 1 are used as sunscreen agents in cosmetic preparations.

10 Claims, No Drawings

ARYLPOLYENECARBOXYLIC ACIDS AND THEIR DERIVATIVES AS SUNSCREEN AGENTS IN COSMETIC PREPARATIONS

The present invention relates to the use of arylpolyenecarboxylic acids and their derivatives of the formula I

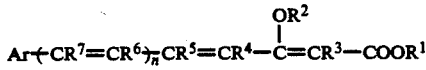

where
Ar is phenyl, biphenylyl or naphthyl, each of which can be substituted by one to three $C_1$–$C_4$-alkyl, $C_1$–$C_4$-alkoxy, hydroxyl or phenoxy groups, or amino groups which can be mono- or di-substituted by $C_1$–$C_4$-alkyl groups, or one methylenedioxy group, it being possible for the substituents to be identical or different,
$R^1$ is hydrogen, an alkali metal or anunoniuxa cation, $C_1$–$C_{20}$-alkyl or $C_2$–$C_{20}$-alkenyl,
$R^2$ is $C_1$–$C_8$-alkyl,
$R^3$ to $R^7$ are each hydrogen or $C_1$–$C_4$-alkyl, and
n is 0 or 1
as sunscreen agents in cosmetic preparations.

Some of the arylpolyenecarboxylic acids and derivatives I are novel compounds.

The present invention also relates to cosmetic preparations containing the compounds I.

The sunscreen agents employed in cosmetic preparations have the task of preventing or at least reducing the consequences of the damaging effects of sunlight on the human skin. However, these sunscreen agents also serve to protect other ingredients from damage or degradation by UV radiation.

The sunlight reaching the surface of the Earth contains UV-B (280 to 320 nm) and UV-A (>320 nm) radiation in the region directly adjacent to that of visible light. The effect on the human skin is made particularly evident in the case of UV-B radiation by sunburn. Accordingly, the industry provides a relatively large number of substances which absorb UV-B radiation and thus prevent sunburn.

Dermatological investigations have now found that UV-A radiation is also perfectly able to cause skin damage by, for example, damaging the keratin or elastin. This reduces the elasticity and water-storage capacity of the skin, ie. it becomes less flexible and tends to wrinkle. The noticeably high incidence of skin cancer in regions of strong sunlight shows that damage to the genetic information in the cells is evidently also caused by sunlight, specifically by UV-A radiation. All these findings thus make it appear necessary to develop efficient filter substances for the UV-A region.

There is a growing demand for sunscreen agents for cosmetic preparations which can be used in particular as UV-A filters and whose absorption maxima ought therefore to be in the region of about 320 to 380 nm. In order to achieve the required effect with the minimal amount of sunscreen agents of this type, they ought additionally to have a high specific extinction. In addition, sunscreen agents for cosmetic products must also meet a large number of other requirements, for example good solubility in cosmetic oils, high stability of the emulsions prepared therewith, high photostability and low intrinsic odor and little intrinsic color.

Thus, DE-A 32 06 586 (1) describes 2-acetyl-5-phenyl-2,4-pentadienoic esters of the formula II

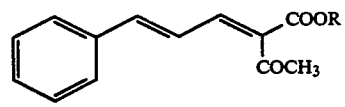

These compounds are recommended as sunscreen agents for cosmetic and industrial uses.

DE-A 27 28 242 (2) relates to cosmetic sunscreen agents for the UV-A region which contain condensates of pyruvic acid or levulinic acid, of the formula III

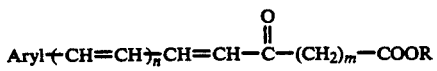

where n is 0 or 1 and m is 0 or 1 or 2.

DE-A 29 45 125 (3) relates to 4-tert-butyl-4'-methoxydibenzoylmethane (IV) and sunscreen agents which contain IV to retard ageing of the skin.

However, the abovementioned requirements for UV filter substances for cosmetic applications are met only conditionally by the compounds II to IV.

It is an object of the present invention to provide sunscreen agents for cosmetic preparations which meet the said requirements to a greater extent than the known agents of this type.

We have found that this object is achieved by the use, defined at the outset, of arylpolyenecarboxylic acids and their derivatives I as sunscreen agents in cosmetic preparations.

Particularly suitable furthermore for the aryl radical is phenyl which can be substituted by one to three $C_1$–$C_4$-alkyl groups, eg. methyl, ethyl, n-propyl, iso-propyl, n-butyl or tert-butyl, or $C_1$–$C_4$-alkoxy groups, eg. methoxy or ethoxy, or one methylenedioxy group or one di($C_1$–$C_4$-alkyl)amino group, eg. dimethylamino or diethylamino.

Examples of Ar which may be mentioned are:
phenyl,
o- or p-tolyl,
p-tert-butyl,
2,3-, 2,4-, 2,5-, 2,6-, 3,4- or 3,5-dimethylphenyl,
mesityl,
o- or p-methoxyphenyl,
2,3-, 2,4-, 2,5-, 2,6-, 3,4- or 3,5-dimethoxyphenyl,
3,4,5-trimethoxyphenyl and
3,4-methylenedioxyphenyl.

$R^1$ is hydrogen or an alkali metal cation, eg. sodium or potassium, or the ammonium cation, or is straight-chain or branched $C_1$–$C_{20}$-alkyl or $C_2$–$C_{20}$-alkenyl. In the first case the compounds are carboxylic acids or salts thereof, and in the latter case they are carboxylic esters.

In a preferred embodiment, $R^1$ is hydrogen or straight-chain or branched $C_1$–$C_8$-alkyl such as methyl, ethyl, n-propyl, iso-propyl, n-butyl, iso-butyl, sec-butyl, tert-butyl, n-pentyl, iso-pentyl, n-hexyl, n-heptyl, n-octyl or 2-ethylhexyl.

$R^2$, which, in the form of β-alkoxy, represents an essential structural feature of the compounds I, is $C_1$–$C_8$-alkyl, preferably $C_1$–$C_4$-alkyl such as methyl, ethyl, n-propyl, iso-propyl, n-butyl, iso-butyl, sec-butyl or tert-butyl.

$R^3$ to $R^7$ are each, independently of one another, hydrogen or $C_1$–$C_4$-alkyl, especially hydrogen or methyl.

The compounds I can be in the form of mixtures of cis and trans isomers in respect of the olefinic double bonds or in the form of the pure isomers.

The following individual substances I are particularly preferred for use as sunscreen agents in cosmetic preparations:

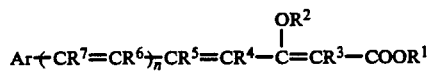

$$Ar-(CR^7=CR^6)_n-CR^5=CR^4-\underset{\underset{OR^2}{|}}{C}=CR^3-COOR^1$$

| Serial No. | Ar | n | $R^1$ | $R^2$ | $R^3$ | $R^4$ | $R^5$ | $R^6$ | $R^7$ |
|---|---|---|---|---|---|---|---|---|---|
| 1 | Phenyl | 0 | H | $CH_3$ | H | H | H | | |
| 2 | 4-Methoxyphenyl | 0 | H | $CH_3$ | H | H | H | | |
| 3 | 4-Methoxyphenyl | 0 | H | $CH_3$ | $CH_3$ | H | H | | |
| 4 | 4-Methoxyphenyl | 0 | $CH_3$ | $CH_3$ | H | H | H | | |
| 5 | 4-Methoxyphenyl | 0 | $C_2H_5$ | $CH_3$ | H | H | H | | |
| 6 | 4-Methoxyphenyl | 0 | n-Propyl | $CH_3$ | H | H | H | | |
| 7 | 4-Methoxyphenyl | 0 | n-Butyl | $CH_3$ | H | H | H | | |
| 8 | 4-Methoxyphenyl | 0 | 2-Ethylhexyl | $CH_3$ | H | H | H | | |
| 9 | 4-Methoxyphenyl | 0 | 2-Ethylhexyl | $CH_3$ | $CH_3$ | H | H | | |
| 10 | 4-Methoxyphenyl | 0 | H | $C_2H_5$ | H | H | H | | |
| 11 | 4-Methoxyphenyl | 0 | $CH_3$ | $C_2H_5$ | H | H | H | | |
| 12 | 4-Methoxyphenyl | 0 | 2-Ethylhexyl | $C_2H_5$ | H | H | H | | |
| 13 | 4-Methoxyphenyl | 0 | H | n-Propyl | H | H | H | | |
| 14 | 4-Methoxyphenyl | 0 | $CH_3$ | n-Propyl | H | H | H | | |
| 15 | 4-Methoxyphenyl | 0 | 2-Ethylhexyl | n-Propyl | H | H | H | | |
| 16 | 3,4-Methylenedioxyphenyl | 0 | H | $CH_3$ | H | H | H | | |
| 17 | 3,4-Methylenedioxyphenyl | 0 | H | $CH_3$ | $CH_3$ | H | H | | |
| 18 | 3,4-Methylenedioxyphenyl | 0 | $CH_3$ | $CH_3$ | H | H | H | | |
| 19 | 3,4-Methylenedioxyphenyl | 0 | $C_2H_5$ | $CH_3$ | H | H | H | | |
| 20 | 3,4-Methylenedioxyphenyl | 0 | n-Propyl | $CH_3$ | H | H | H | | |
| 21 | 3,4-Methylenedioxyphenyl | 0 | n-Butyl | $CH_3$ | H | H | H | | |
| 22 | 3,4-Methylenedioxyphenyl | 0 | 2-Ethylhexyl | $CH_3$ | H | H | H | | |
| 23 | 3,4-Methylenedioxyphenyl | 0 | H | $C_2H_5$ | H | H | H | | |
| 24 | 3,4-Methylenedioxyphenyl | 0 | $CH_3$ | $C_2H_5$ | H | H | H | | |
| 25 | 3,4-Methylenedioxyphenyl | 0 | 2-Ethylhexyl | $C_2H_5$ | H | H | H | | |
| 26 | 4-(Dimethylamino)phenyl | 0 | H | $CH_3$ | H | H | H | | |
| 27 | 4-(Dimethylamino)phenyl | 0 | H | $CH_3$ | $CH_3$ | H | H | | |
| 28 | 4-(Dimethylamino)phenyl | 0 | $CH_3$ | $CH_3$ | H | H | H | | |
| 29 | 4-(Dimethylamino)phenyl | 0 | $C_2H_5$ | $CH_3$ | H | H | H | | |
| 30 | 4-(Dimethylamino)phenyl | 0 | n-Propyl | $CH_3$ | H | H | H | | |
| 31 | 4-(Dimethylamino)phenyl | 0 | n-Butyl | $CH_3$ | H | H | H | | |
| 32 | 4-(Dimethylamino)phenyl | 0 | 2-Ethylhexyl | $CH_3$ | H | H | H | | |
| 33 | 4-(Dimethylamino)phenyl | 0 | H | $C_2H_5$ | H | H | H | | |
| 34 | 4-(Dimethylamino)phenyl | 0 | $CH_3$ | $C_2H_5$ | H | H | H | | |
| 35 | 4-(Dimethylamino)phenyl | 0 | 2-Ethylhexyl | $C_2H_5$ | H | H | H | | |
| 36 | 4-tert.-Butylphenyl | 0 | H | $CH_3$ | H | H | H | | |
| 37 | 4-Methoxyphenyl | 0 | H | $CH_3$ | H | $CH_3$ | H | | |
| 38 | Phenyl | 1 | H | $CH_3$ | H | H | H | H | H |
| 39 | Phenyl | 1 | H | $CH_3$ | H | H | H | H | $CH_3$ |
| 40 | Phenyl | 1 | H | $CH_3$ | H | H | H | $CH_3$ | H |
| 41 | Phenyl | 1 | H | $CH_3$ | H | H | $CH_3$ | H | H |
| 42 | Phenyl | 1 | H | $CH_3$ | H | $CH_3$ | H | H | H |
| 43 | Phenyl | 1 | H | $CH_3$ | $CH_3$ | H | H | H | H |
| 44 | Phenyl | 1 | $CH_3$ | $CH_3$ | H | H | H | H | H |
| 45 | Phenyl | 1 | $C_2H_5$ | $CH_3$ | H | H | H | H | H |
| 46 | Phenyl | 1 | n-Propyl | $CH_3$ | H | H | H | H | H |
| 47 | Phenyl | 1 | n-Butyl | $CH_3$ | H | H | H | H | H |
| 48 | Phenyl | 1 | 2-Ethylhexyl | $CH_3$ | H | H | H | H | H |
| 49 | Phenyl | 1 | H | $C_2H_5$ | H | H | H | H | H |
| 50 | Phenyl | 1 | $CH_3$ | $C_2H_5$ | H | H | H | H | H |
| 51 | Phenyl | 1 | 2-Ethylhexyl | $C_2H_5$ | H | H | H | H | H |
| 52 | Phenyl | 1 | H | n-Propyl | H | H | H | H | H |
| 53 | Phenyl | 1 | $CH_3$ | n-Propyl | H | H | H | H | H |
| 54 | Phenyl | 1 | 2-Ethylhexyl | n-Propyl | H | H | H | H | H |
| 55 | 4-Methoxyphenyl | 1 | H | $CH_3$ | H | H | H | H | H |
| 56 | 4-Methoxyphenyl | 1 | H | $CH_3$ | H | H | H | H | $CH_3$ |
| 57 | 4-Methoxyphenyl | 1 | H | $CH_3$ | H | H | H | $CH_3$ | H |
| 58 | 4-Methoxyphenyl | 1 | H | $CH_3$ | H | H | $CH_3$ | H | H |
| 59 | 4-Methoxyphenyl | 1 | H | $CH_3$ | H | $CH_3$ | H | H | H |
| 60 | 4-Methoxyphenyl | 1 | H | $CH_3$ | $CH_3$ | H | H | H | H |
| 61 | 4-Methoxyphenyl | 1 | $CH_3$ | $CH_3$ | H | H | H | H | H |
| 62 | 4-Methoxyphenyl | 1 | $C_2H_5$ | $CH_3$ | H | H | H | H | H |
| 63 | 4-Methoxyphenyl | 1 | n-Propyl | $CH_3$ | H | H | H | H | H |
| 64 | 4-Methoxyphenyl | 1 | n-Butyl | $CH_3$ | H | H | H | H | H |
| 65 | 4-Methoxyphenyl | 1 | 2-Ethylhexyl | $CH_3$ | H | H | H | H | H |
| 66 | 4-Methoxyphenyl | 1 | H | $C_2H_5$ | H | H | H | H | H |

The following individual substances I are particularly preferred for use as sunscreen agents in cosmetic preparations:

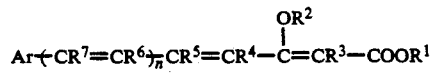

$$Ar\mathrm{-(CR^7=CR^6)}_n\mathrm{-CR^5=CR^4-}\underset{\underset{OR^2}{|}}{C}\mathrm{=CR^3-COOR^1}$$

| Serial No. | Ar | n | $R^1$ | $R^2$ | $R^3$ | $R^4$ | $R^5$ | $R^6$ | $R^7$ |
|---|---|---|---|---|---|---|---|---|---|
| 67 | 4-Methoxyphenyl | 1 | $CH_3$ | $C_2H_5$ | H | H | H | H | H |
| 68 | 4-Methoxyphenyl | 1 | 2-Ethylhexyl | $C_2H_5$ | H | H | H | H | H |
| 69 | 4-Methoxyphenyl | 1 | $CH_3$ | $CH_3$ | H | H | H | $CH_3$ | H |
| 70 | 4-Methoxyphenyl | 1 | $C_2H_5$ | $CH_3$ | H | H | H | $CH_3$ | H |
| 71 | 4-Methoxyphenyl | 1 | n-Propyl | $CH_3$ | H | H | H | $CH_3$ | H |
| 72 | 4-Methoxyphenyl | 1 | n-Butyl | $CH_3$ | H | H | H | $CH_3$ | H |
| 73 | 4-Methoxyphenyl | 1 | 2-Ethylhexyl | $CH_3$ | H | H | H | $CH_3$ | H |
| 74 | 4-Methoxyphenyl | 1 | H | $C_2H_5$ | H | H | H | $CH_3$ | H |
| 75 | 4-Methoxyphenyl | 1 | $CH_3$ | $C_2H_5$ | H | H | H | $CH_3$ | H |
| 76 | 4-Methoxyphenyl | 1 | 2-Ethylhexyl | $C_2H_5$ | H | H | H | $CH_3$ | H |
| 77 | 4-Methoxyphenyl | 1 | H | n-Propyl | H | H | H | H | H |
| 78 | 4-Methylphenyl | 1 | $CH_3$ | $CH_3$ | H | H | H | H | H |
| 79 | 4-tert.-Butylphenyl | 1 | H | $CH_3$ | H | H | H | H | H |
| 80 | 4-tert.-Butylphenyl | 1 | H | $CH_3$ | H | H | H | H | $CH_3$ |
| 81 | 4-tert.-Butylphenyl | 1 | H | $CH_3$ | H | H | H | $CH_3$ | H |
| 82 | 4-tert.-Butylphenyl | 1 | H | $CH_3$ | H | H | $CH_3$ | H | H |
| 83 | 4-tert.-Butylphenyl | 1 | H | $CH_3$ | H | $CH_3$ | H | H | H |
| 84 | 4-tert.-Butylphenyl | 1 | H | $CH_3$ | $CH_3$ | H | H | H | H |
| 85 | 4-tert.-Butylphenyl | 1 | $CH_3$ | $CH_3$ | H | H | H | H | H |
| 86 | 4-tert.-Butylphenyl | 1 | $C_2H_5$ | $CH_3$ | H | H | H | H | H |
| 87 | 4-tert.-Butylphenyl | 1 | n-Propyl | $CH_3$ | H | H | H | H | H |
| 88 | 4-tert.-Butylphenyl | 1 | n-Butyl | $CH_3$ | H | H | H | H | H |
| 89 | 4-tert.-Butylphenyl | 1 | 2-Ethylhexyl | $CH_3$ | H | H | H | H | H |
| 90 | 4-tert.-Butylphenyl | 1 | H | $C_2H_5$ | H | H | H | H | H |
| 91 | 4-tert.-Butylphenyl | 1 | $CH_3$ | $C_2H_5$ | H | H | H | H | H |
| 92 | 4-tert.-Butylphenyl | 1 | 2-Ethylhexyl | $C_2H_5$ | H | H | H | H | H |
| 93 | 4-tert.-Butylphenyl | 1 | H | n-Propyl | H | H | H | H | H |
| 94 | 4-tert.-Butylphenyl | 1 | $CH_3$ | n-Propyl | H | H | H | H | H |
| 95 | 4-tert.-Butylphenyl | 1 | 2-Ethylhexyl | n-Propyl | H | H | H | H | H |
| 96 | 4-tert.-Butylphenyl | 1 | H | $CH_3$ | H | H | H | $CH_3$ | H |
| 97 | 4-tert.-Butylphenyl | 1 | $CH_3$ | $CH_3$ | H | H | H | $CH_3$ | H |
| 98 | 4-tert.-Butylphenyl | 1 | $C_2H_5$ | $CH_3$ | H | H | H | $CH_3$ | H |
| 99 | 4-tert.-Butylphenyl | 1 | n-Propyl | $CH_3$ | H | H | H | $CH_3$ | H |
| 100 | 4-tert.-Butylphenyl | 1 | n-Butyl | $CH_3$ | H | H | H | $CH_3$ | H |
| 101 | 4-tert.-Butylphenyl | 1 | H | $C_2H_5$ | H | H | H | $CH_3$ | H |
| 102 | 4-tert.-Butylphenyl | 1 | $CH_3$ | $C_2H_5$ | H | H | H | $CH_3$ | H |
| 103 | 4-tert.-Butylphenyl | 1 | $C_2H_5$ | $C_2H_5$ | H | H | H | $CH_3$ | H |
| 104 | 4-tert.-Butylphenyl | 1 | n-Propyl | $C_2H_5$ | H | H | H | $CH_3$ | H |
| 105 | 4-tert.-Butylphenyl | 1 | 2-Ethylphenyl | $C_2H_5$ | H | H | H | $CH_3$ | H |
| 106 | 4-tert.-Butylphenyl | 1 | H | n-Propyl | H | H | H | $CH_3$ | H |
| 107 | 4-tert.-Butylphenyl | 1 | $CH_3$ | n-Propyl | H | H | H | $CH_3$ | H |
| 108 | 4-tert.-Butylphenyl | 1 | $C_2H_5$ | n-Propyl | H | H | H | $CH_3$ | H |
| 109 | 4-tert.-Butylphenyl | 1 | n-Propyl | n-Propyl | H | H | H | $CH_3$ | H |
| 110 | 4-tert.-Butylphenyl | 1 | 2-Ethylhexyl | n-Propyl | H | H | H | $CH_3$ | H |
| 111 | 4-Methoxyphenyl | 1 | $CH_3$ | $CH_3$ | H | $CH_3$ | H | H | H |
| 112 | 4-Methoxyphenyl | 1 | iso-Propyl | $CH_3$ | H | H | H | H | H |
| 113 | 4-Methoxyphenyl | 1 | n-Pentyl | $CH_3$ | H | H | H | H | H |
| 114 | 4-Methoxyphenyl | 1 | iso-Butyl | $CH_3$ | H | H | H | H | H |
| 115 | 4-Methoxyphenyl | 1 | sec.-Butyl | $CH_3$ | H | H | H | H | H |
| 116 | 4-Methoxyphenyl | 1 | $C_2H_5$ | $C_2H_5$ | H | H | H | H | H |
| 117 | 4-Methoxyphenyl | 1 | n-Propyl | $C_2H_5$ | H | H | H | H | H |
| 118 | 4-Methoxyphenyl | 1 | iso-Propyl | $C_2H_5$ | H | H | H | H | H |
| 119 | 4-Methoxyphenyl | 1 | n-Butyl | $C_2H_5$ | H | H | H | H | H |
| 120 | 4-Methoxyphenyl | 1 | iso-Butyl | $C_2H_5$ | H | H | H | H | H |
| 121 | 4-Methoxyphenyl | 1 | sec.-Butyl | $C_2H_5$ | H | H | H | H | H |
| 122 | 4-Methoxyphenyl | 1 | $CH_3$ | n-Propyl | H | H | H | H | H |
| 123 | 4-Methoxyphenyl | 1 | $C_2H_5$ | n-Propyl | H | H | H | H | H |
| 124 | 4-Methoxyphenyl | 1 | n-Propyl | n-Propyl | H | H | H | H | H |
| 125 | 4-Methoxyphenyl | 1 | iso-Propyl | n-Propyl | H | H | H | H | H |
| 126 | 4-Methoxyphenyl | 1 | n-Butyl | n-Propyl | H | H | H | H | H |
| 127 | 4-Methoxyphenyl | 1 | H | iso-Propyl | H | H | H | H | H |
| 128 | 4-Methoxyphenyl | 1 | $CH_3$ | iso-Propyl | H | H | H | H | H |
| 129 | 4-Methoxyphenyl | 1 | $C_2H_5$ | iso-Propyl | H | H | H | H | H |
| 130 | 4-Methoxyphenyl | 1 | n-Propyl | iso-Propyl | H | H | H | H | H |
| 131 | 4-Methoxyphenyl | 0 | H | $CH_3$ | H | H | $CH_3$ | | |
| 132 | 4-Methoxyphenyl | 0 | $CH_3$ | $CH_3$ | $CH_3$ | H | H | | |
| 133 | 4-Methoxyphenyl | 0 | $CH_3$ | $CH_3$ | H | $CH_3$ | H | | |

Some of the arylpolyenecarboxylic acids and their derivatives I are novel compounds. The present invention therefore also relates to arylpolyenecarboxylic acids and their derivatives of the formula Ia

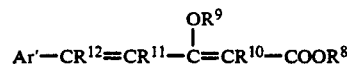   Ia where Ar and Ar′, $R^1$ and $R^8$, $R^2$ and $R^9$, and $R^3$ and $R^5$ amd $R^{10}$ to $R^{12}$ have the same meaning, with the exception of the following individual compounds for the arylpolyenecarboxylic acids and derivatives Ia:

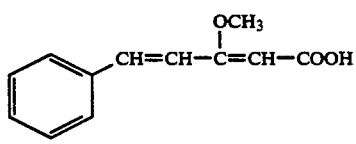

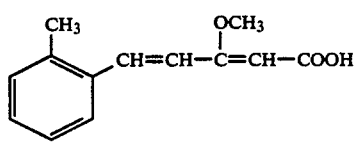

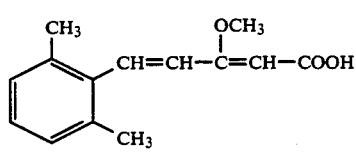

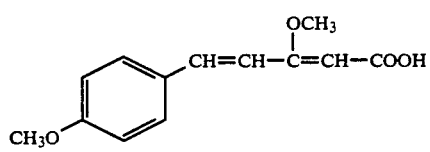

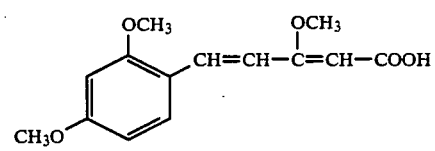

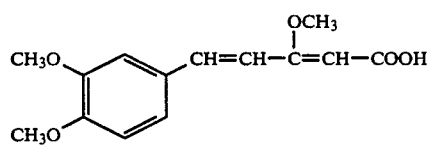

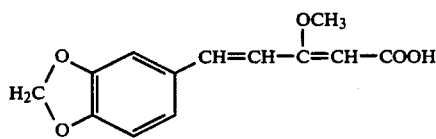

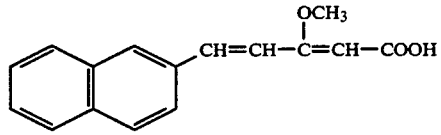

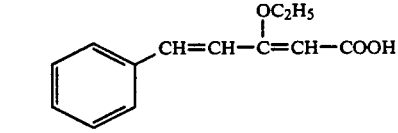

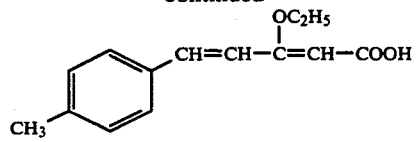

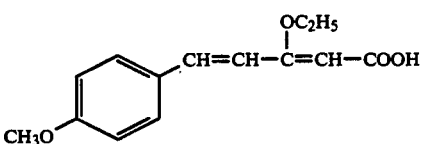

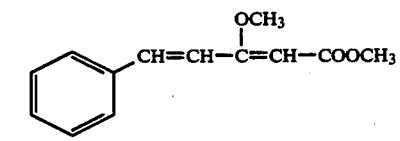

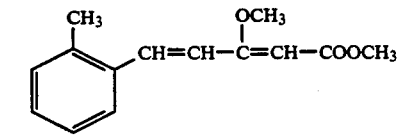

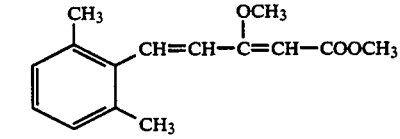

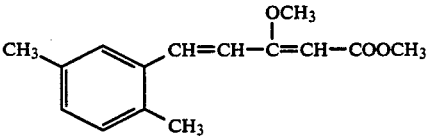

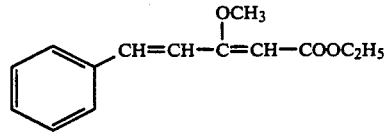

The present invention also relates to arylpolyenecarboxylic acids and their derivatives of the formula Ib

   Ib where Ar and Ar″, $R^1$ and $R^{13}$, $R^2$ and $R^{14}$, and $R^3$ to $R^7$ and $R^{15}$ to $R^{19}$ have the same meaning, with the exception of the following individual compounds for the arylpolyenecarboxylic acids and derivatives Ib:

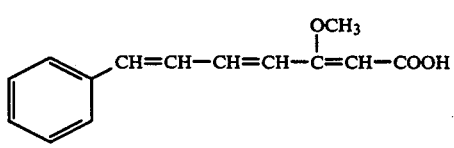

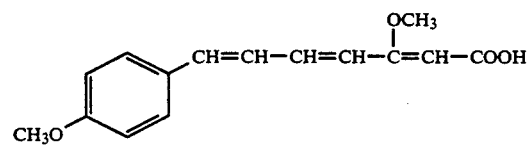

-continued

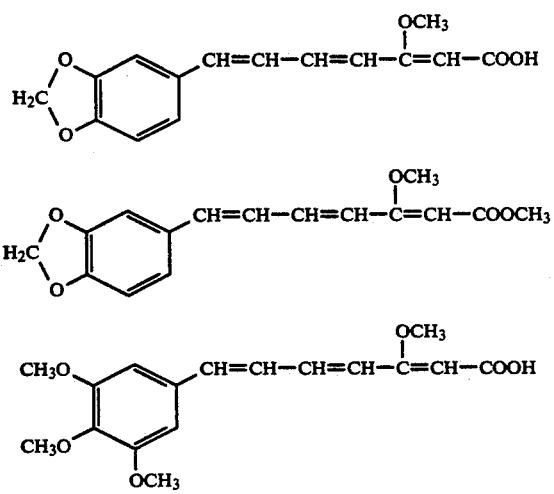

Of particular interest are those novel arylpolyenecarboxylic acids and derivatives Ia and Ib which are Nos. 1 to 133 in the list of individual substances, but especially those which are mentioned as experimental examples with melting point and spectroscopic data.

The novel compounds I are expediently prepared by aldol condensation of an aldehyde or ketone of the formula IV

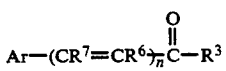    IV with a β-alkoxy carboxylic acid derivative of the formula V

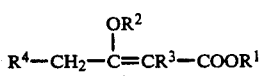    V in a conventional manner under basic conditions.

Depending on how the reaction is carried out, as a rule there is initial formation of the free acids or the salts thereof ($R^1$=hydrogen or an alkali metal or ammonium cation), which can then be derivatized by conventional reactions with the appropriate alcohols to give esters ($R^1$=$C_1$-$C_{20}$-alkyl or $C_2$-$C_{20}$-alkenyl).

The aldol condensation is normally carried out in an inert organic solvent such as a hydrocarbon, eg. toluene or xylene, or an ether, eg. diethyl ether, methyl tert-butyl ether, diisopropyl ether, tetrahydrofuran or dioxane. Examples of suitable bases are sodium hydride. sodamide, lithium diisopropylaxeide, sodium methylate, sodium ethylate or potassium tert-butylate. The reaction is normally carried out at from 0° to 150° C., preferably from 20° to 100° C., in particular from 40° to 80° C., usually under atmospheric pressure.

The compounds I to be used according to the invention act as sunscreen agents in cosmetic preparations for preventive care. Sunscreen products of this type can be in the form of liquids, pastes or solids, for example as water-in-oil creams, oil-in water creams and lotions, aerosol creams, gels, oils, grease pencils, dusting powders, sprays or alcoholic-aqueous lotions.

The present invention also relates to cosmetic preparations which contain from 0.1 to 10% by weight, preferably 1 to 7% by weight, based on the total amount of the cosmetic preparation, of one or more of the compounds I as sunscreen agents, where the compounds I are employed in conventional excipients or diluents, for example as solution in an oil.

Examples of conventional oil components in cosmetics are liquid paraffin, glyceryl stearate, isopropyl myristate, diisopropyl adipate, cetylstearyl 2-ethylhexanoate, hydrogenated polyisobutene, petrolatum, caprylic acid/capric acid triglycerides, microcrystalline wax, lanolin and stearic acid.

Other conventional sunscreen agents such as
2-hydroxy-4-methoxybenzophenone,
2-hydroxy-4-methoxybenzophenone-5-sulfonic acid,
ethyl p-aminobenzoate reacted with 25 moles of ethylene oxide,
2-ethylhexyl p-methoxycinnamate,
2-ethylhexyl p-(N,N-dimethylamino)benzoate,
2-phenylbenzimidazole-5-sulfonic acid,
3-(4-methylbenzylidene)camphor or
2,4,6-tri(p-[2-ethylhexoxycarbonyl)anilino]-1,3,5-triazine can be used in the amounts conventional for this purpose together with the compounds I.

Examples of conventional cosmetic auxiliaries suitable as additives are emulsifiers such as fatty alcohol ethoxylates, sorbitan fatty acid esters or lanolin derivatives, thickeners such as carboxymethylcellulose or crosslinked polyacrylic acid, preservatives and perfumes.

The arylpolyenecarboxylic acids and their derivatives I to be used according to the invention usually have a particularly high absorptive power, especially in the UV-A region, which is evident on comparison with the extinctions of the novel compounds I with, for example, the extinctions of typical representatives of the compounds II to IV. They can also be advantageously used in combination with UV-B filter substances. Furthermore, they are readily soluble in cosmetic oils and can easily be incorporated in cosmetic formulations. The emulsions prepared with the compounds I have particularly high stability, and the compounds I themselves have high photostability, which is evident on comparison of the photostabilities of the novel compounds I with, for example, the photostabilities of typical representatives of the compounds II to IV, and the preparations produced with I have a pleasant feeling on the skin.

The compounds I are virtually colorless and odorless. UV-A filter substances currently commercially available are yellow and tend, moreover, to stain items of clothing. This can be avoided by using the novel compounds.

PREPARATION EXAMPLES

3-Methoxy-7-(4-methoxyphenyl)-2,4,6-heptatrienoic acid (No. 55 in the list of particularly preferred individual compounds)

16.5 g of an 80% by weight suspension of sodium hydride in white oil (corresponding to 0.55 mol of NaH) were mixed with 500 ml of anhydrous tetrahydrofuran and, while stirring efficiently at 50° to 60° C., a mixture of 81 g (corresponding to 0.5 mol) of p-methoxycinnamaldehyde and 65 g (corresponding to 0.5 mol) of methyl β-methoxycrotonate was added dropwise. The rate of this dropwise addition was chosen so that the mixture continued to boil gently. It was then stirred at 65° C. for 3 hours and subsequently at room temperature overnight. To work up the reaction mixture was cooled and mixed with 0.5 l of ice-water and then extracted with methyl tertbutyl ether. The remaining alkaline aqueous phase was acidified with dilute hydrochloric acid while cooling in ice, and the precipitate was filtered off and thoroughly washed with water. Drying resulted in 83 g of the title compound of melting point 187° C. (after recrystallization from ethyl acetate), corresponding to a yield of 64%.

The following compounds in the list of particularly preferred individual compounds were prepared in a similar manner to the procedure indicated above. The following table includes the longest wavelength maxima $\lambda_{max}$ and the extinctions E (1% by weight solution, path length 1 cm) of the compounds. These are compared with the corresponding values for compound A from reference (1), compound B from reference (2) and compound C from reference (3).

| No. | Structure of the compound | Melting point [°C] | $\lambda_{max}$ [nm] | $E_{1cm}^{1\%}$ |
|---|---|---|---|---|
| 2 | 4-CH$_3$O-C$_6$H$_4$-CH=CH-C(OCH$_3$)=CH-COOH | 173 | 324 | 1184 |
| 3 | 4-CH$_3$O-C$_6$H$_4$-CH=CH-C(OCH$_3$)=C(CH$_3$)-COOH | 116 | 320 | 1019 |
| 4 | 4-CH$_3$O-C$_6$H$_4$-CH=CH-C(OCH$_3$)=CH-COOCH$_3$ | 83 | 329 | 1149 |
| 16 | 3,4-methylenedioxy-C$_6$H$_3$-CH=CH-C(OCH$_3$)=CH-COOH | 156 | 337 | 984 |
| 18 | 3,4-methylenedioxy-C$_6$H$_3$-CH=CH-C(OCH$_3$)=CH-COOCH$_3$ | 108 | 341 | 909 |
| 36 | 4-(CH$_3$)$_3$C-C$_6$H$_4$-CH=CH-C(OCH$_3$)=CH-COOH | 202 | 312 | 1158 |
| 38 | C$_6$H$_5$-CH=CH-CH=CH-C(OCH$_3$)=CH-COOH | 190 | 329 | 1937 |
| 44 | C$_6$H$_5$-CH=CH-CH=CH-C(OCH$_3$)=CH-COOCH$_3$ | (oil) | 334 | 1699 |
| 55 | 4-CH$_3$O-C$_6$H$_4$-CH=CH-CH=CH-C(OCH$_3$)=CH-COOH | 187 | 346 | 1651 |

-continued

| No. | Structure of the compound | Melting point [°C.] | $\lambda_{max}$ [nm] | $E_{1cm}^{1\%}$ |
|---|---|---|---|---|
| 57 | CH₃O–C₆H₄–CH=C(CH₃)–CH=CH–C(OCH₃)=CH–COOH | 158 | 334 | 1451 |
| 61 | CH₃O–C₆H₄–CH=CH–CH=CH–C(OCH₃)=CH–COOCH₃ | 126 | 351 | 1655 |
| 62 | CH₃O–C₆H₄–CH=CH–CH=CH–C(OCH₃)=CH–COOC₂H₅ | 46 | 351 | 1544 |
| 63 | CH₃O–C₆H₄–CH=CH–CH=CH–C(OCH₃)=CH–COOCH₂CH₂CH₃ | 45 | 351 | 1400 |
| 64 | CH₃O–C₆H₄–CH=CH–CH=CH–C(OCH₃)=CH–COOCH₂CH₂CH₂CH₃ | 55 | 351 | 1308 |
| 65 | CH₃O–C₆H₄–CH=CH–CH=CH–C(OCH₃)=CH–COOCH₂CH(C₂H₅)(CH₂CH₂CH₂CH₃) | (oil) | 351 | 1170 |
| 66 | CH₃O–C₆H₄–CH=CH–CH=CH–C(OC₂H₅)=CH–COOH | 152 | 347 | 1610 |
| 69 | CH₃O–C₆H₄–CH=C(CH₃)–CH=CH–C(OCH₃)=CH–COOCH₃ | 98 | 340 | 1358 |
| 77 | CH₃O–C₆H₄–CH=CH–CH=CH–C(OCH₂CH₂CH₃)=CH–COOH | 128 | 350 | 1438 |
| 78 | CH₃–C₆H₄–CH=CH–CH=CH–C(OCH₃)=CH–COOCH₃ | 175 | 347 | 1291 |

| No. | Structure of the compound | Melting point [°C] | $\lambda_{max}$ [nm] | $E_{1cm}^{1\%}$ |
|---|---|---|---|---|
| 96 | (CH₃)₃C—C₆H₄—CH=C(CH₃)—CH=CH—C(OCH₃)=CH—COOH | 182 | 326 | 1412 |
| 97 | (CH₃)₃C—C₆H₄—CH=C(CH₃)—CH=CH—C(OCH₃)=CH—COOCH₃ | 165 | 328 | 1285 |
| 112 | CH₃O—C₆H₄—CH=CH—CH=CH—C(OCH₃)=CH—COOCH(CH₃)—CH₃ | 65 | 351 | 1382 |
| 131 | CH₃O—C₆H₄—C(CH₃)=CH—C(OCH₃)=CH—COOH | 130 | 305 | 702 |
| 133 | CH₃O—C₆H₄—CH=C—C(OCH₃)(CH₃)=CH—COOCH₃ | (oil) | 331 | 1009 |

| For comparison: No. | Structure of the compound | Melting point [°C] | $\lambda_{max}$ [nm] | $E_{1cm}^{1\%}$ |
|---|---|---|---|---|
| A | C₆H₅—CH=CH—CH=C(COCH₃)—COOC₂H₅ | 83 | 329 | 1261 |
| B | C₆H₅—CH=CH—CO—COOH | 127 | 344 | 915 |
| C | (CH₃)₃C—C₆H₄—CO—CH₂—CO—C₆H₄—OCH₃ | 81 | 352 | 1140 |

The compounds to be used according to the invention have a higher photostability than the prior art agents. Thus, the activity of compound No. 38 remaining after irradiation for 2 hours is 90% and after irradiation for 8 hours is 80%, whereas the activity of compounds A and B remaining after irradiation for only 2 hours is only 30% and less than 10%, respectively, and that of compound C after irradiation for 6 hours is 51%. The activity remaining was determined by irradiating an ethanolic solution containing 10 mg/l of the compound in a Heraeus Suntest ®, which contains a xenon lamp as radiation source, and investigating the content after the stated times.

We claim:

1. A sunscreen composition comprising a cosmetic carrier and 0.1–10% by weight of a compound of the formula:

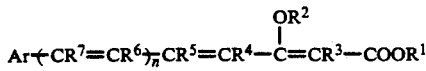

wherein:
Ar is phenyl, biphenylyl or naphthyl, each of which is unsubstituted or substituted by one to three independently selected $C_1$-$C_4$-alkyl, $C_1$-$C_4$-alkoxy, hydroxyl, phenoxy, amino, $C_1$-$C_4$-alkylamino, or di-($C_1$-$C_4$-alkyl)amino groups, or by one methylenedioxy group,
$R^1$ is hydrogen, alkali metal cation, ammonium, $C_1$-$C_{20}$-alkyl or $C_2$-$C_{20}$-alkenyl,
$R^2$ is $C_1$-$C_8$-alkyl,
$R^3$ to $R^7$ are each hydrogen or $C_1$-$C_4$-alkyl, and
n is 0 or 1.

2. A sunscreen cosmetic composition as claimed in claim 1, wherein:
Ar is phenyl which is unsubstituted or substituted by one to three $C_1$-$C_4$-alkyl or $C_1$-$C_4$-alkoxy groups, one methylenedioxy group, or one di($C_1$-$C_4$-alkyl)amino group,
$R^1$ is hydrogen or $C_1$-$C_8$-alkyl,
$R^2$ is $C_1$-$C_4$-alkyl,
$R^3$ to $R^7$ are each hydrogen or methyl, and
n is 0 or 1.

3. A sunscreen cosmetic composition according to claim 1, wherein said compound of the formula I is present in an amount of 1-7% by weight.

4. A sunscreen cosmetic composition according to claim 1, wherein said compound of formula I is 3-methoxy-7-(4-methoxyphenyl) -2,4,6-heptatrienoic acid.

5. A sunscreen cosmetic composition according to claim 1, further comprising one or more members selected from the group consisting of cosmetic excipients, diluents, emulsifiers, thickeners, preservatives, and perfumes.

6. A sunscreen method comprising applying a sunscreen cosmetic composition according to claim 1 to the skin in a sunscreen-effective amount.

7. A sunscreen method comprising applying a sunscreen cosmetic composition according to claim 2 to the skin in a sunscreen-effective amount.

8. A sunscreen method comprising applying a sunscreen cosmetic composition according to claim 3 to the skin in a sunscreen-effective amount.

9. A sunscreen method comprising applying a sunscreen cosmetic composition according to claim 4 to the skin in a sunscreen-effective amount.

10. A sunscreen method comprising applying a sunscreen cosmetic composition according to claim 5 to the skin in a sunscreen-effective amount.

* * * * *